United States Patent [19]
Manzo et al.

[11] Patent Number: 5,395,936
[45] Date of Patent: Mar. 7, 1995

[54] 7-(4-[4-AMINOPHENYL)SULPHONYL]-1-PIPERAZINYL FLUORQUINOLONIC DERIVATIVES AND SYNTHESIS

[76] Inventors: Ruben H. Manzo; Daniel A. Allemandi; Jorge D. Perez, all of University of Chemistry, 22 Velez Sarsfield Avenue, (5016) Cordoba, Province of Cordoba, Argentina

[21] Appl. No.: 71,638

[22] Filed: Jun. 4, 1993

[51] Int. Cl.⁶ ............... C07D 401/00; A01N 43/58; A01N 43/60
[52] U.S. Cl. ................................................ 544/363
[58] Field of Search ........................ 544/363; 514/254

[56] References Cited

U.S. PATENT DOCUMENTS

| | | |
|---|---|---|
| 4,559,341 | 12/1985 | Petersen et al. ............. 514/254 |
| 4,782,061 | 11/1988 | Kruse et al. ................ 514/254 |
| 4,980,353 | 12/1990 | Grohe et al. ............... 514/254 |

*Primary Examiner*—Douglas W. Robinson
*Assistant Examiner*—S. Saucier
*Attorney, Agent, or Firm*—Keck, Mahin & Cate

[57] ABSTRACT

The present invention relates to novel compounds of 7-(4-[4-aminophenyl)sulphonyl]-1-piperazinyl) fluorquinolonic derivatives, of the formula:

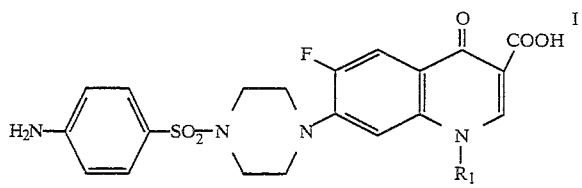

wherein $R_1$ represents $C_1-C_3$ alkyl, and are denominated N-sulphanilyl-derivatives. They are obtained by the process of the invention from the 7-(1-piperazinyl) fluorquinolonic compounds and their esters.

2 Claims, No Drawings

7-(4-[4-AMINOPHENYL)SULPHONYL]-1-PIPERAZINYL FLUORQUINOLONIC DERIVATIVES AND SYNTHESIS

FIELD OF THE INVENTION

This invention is related to novel compounds and a process of preparing them whereby such compounds show pharmacological activity, and are 7-(4-[4-aminophenyl)sulphonyl]-1-piperazinyl) fluorquinolonic derivatives, having the formula:

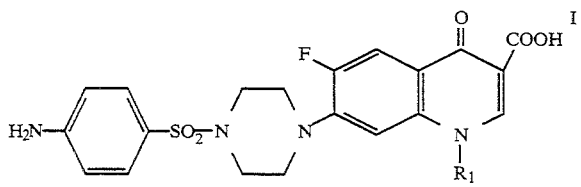

wherein $R_1$ represents $C_1$–$C_6$ alkyl.

They are denominated N-sulphanilyl-derivatives and are obtained from 7-(1-piperazinyl)fluorquinolonic compounds and their esters.

BACKGROUND OF THE INVENTION

The compounds of this invention have not been disclosed in literature, but their antibacterial fluorinated quinolone precursors or original products are known, like the Ciprofloxacine (CFXM), from: K Grohe et al., Ger pat. 3,142,854, and U.S. Pat. No. 4,670,444 (1983, 1987 both to Bayer A. G.); K. Grohe, H. Heitzer, Ann. 1987, 29; and the Norfloxacine from: T. Irikura, Belg. pat. 863,429 and U.S. Pat. No. 4,146,719 (1978, 1979 both to Kyorin); M. Pesson, Ger pat. 2,840,910 and U.S. Pat. No. 4,292,317 (1979, 1981 to Roger Bellon/Dainippon); H. Koga et al., J. Med. Chem. 23, 1358 (1980).

SUMMARY OF THE INVENTION

A process of chemical synthesis is described, through which, 7-(4-[4-aminophenyl)sulphonyl]-1-piperazinyl) fluorquinolonic derivatives, denominated N-sulphanilyl-derivatives, were prepared from 7-(1-piperazinyl) fluorquinolonic antimicrobial agents. The N-sulphanily derivatives are new molecules that show an antimicrobial activity in vitro, significantly larger than the activity of their precursors against Gram-positive bacteria. The object of the invention is the preparation of new antimicrobial fluorquinolonic agents, whose finality is to provide better antimicrobial fluorquinolonic agents with therapeutic utility.

DETAILED DESCRIPTION OF THE PREFERRED EMBODIMENTS

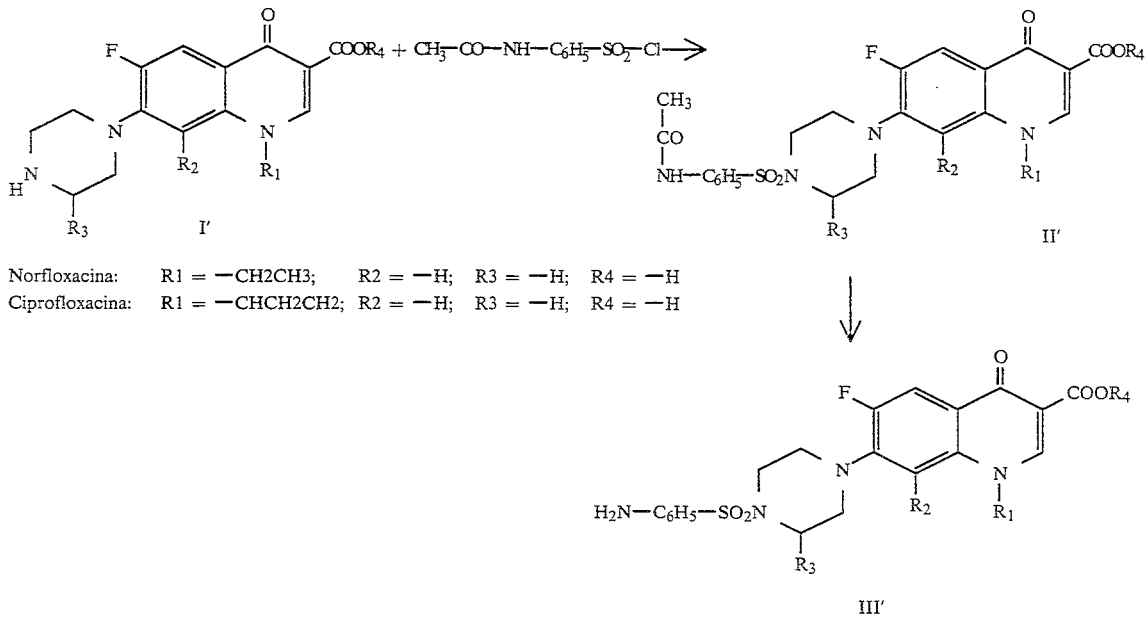

Norfloxacina: $R_1 = -CH_2CH_3$; $R_2 = -H$; $R_3 = -H$; $R_4 = -H$
Ciprofloxacina: $R_1 = -CHCH_2CH_2$; $R_2 = -H$; $R_3 = -H$; $R_4 = -H$ The N-sulphanilyl-derivatives (III') were prepared starting from the 7-(1-piperazinyl)fluorquinolonic agents or their esters (I'), by reaction with N-acetylsulphanilyl chloride, producing the intermediate compounds (II'), which lead to the final products (III') by hydrolysis.

In an erlenmeyer supported on a heating pad provided with magnetic stirrer, 0,32 mmol of compound (I) as powder were suspended in 5 ml of distilled and dried acetone; then 81.5 mg (0,35 mmol) of N-acetylsulphanilyl chloride were added. After supporting a refrigerator on the nozzle of the erlenmeyer, the mixture was heated to boiling during 30 minutes. After cooling, the solid residue was isolated by filtration and then dried.

The obtained product was introduced into an appropriate vessel, added 10 ml of a 2N aqueous solution of sodium hydroxide and maintained to boiling at reflux during 2 hours. After cooling, the solution was neutralized with hydrochloric acid to 10%, the isolated solid was filtered, and washed with water, dried, and finally the corresponding compound (III) was obtained.

EXAMPLE 1

The compound (III'), that is the, 7-fluor-1,4-dihydro-7-(4-[(4-aminophenyl)sulphonyl]-1-piperazinyl)-4-oxo-3-quinoline carboxylic acid was obtained with mol yield of 85% when compound (I') was the 1-ethyl-6-fluor-1,4-dihydro-7 (1-piperazinyl)-4-oxo-3-quinoline carboxylic acid, INN 4622 (Norfioxacine) CAS 70458-96-7. The compound (III') was recrystallized from a mixture of dimethylformamide, ethanol and water (5:5:1) with a yield of 95% producing a yellowish white solid insoluble in water, but soluble in a solution of alkaline hydroxides.

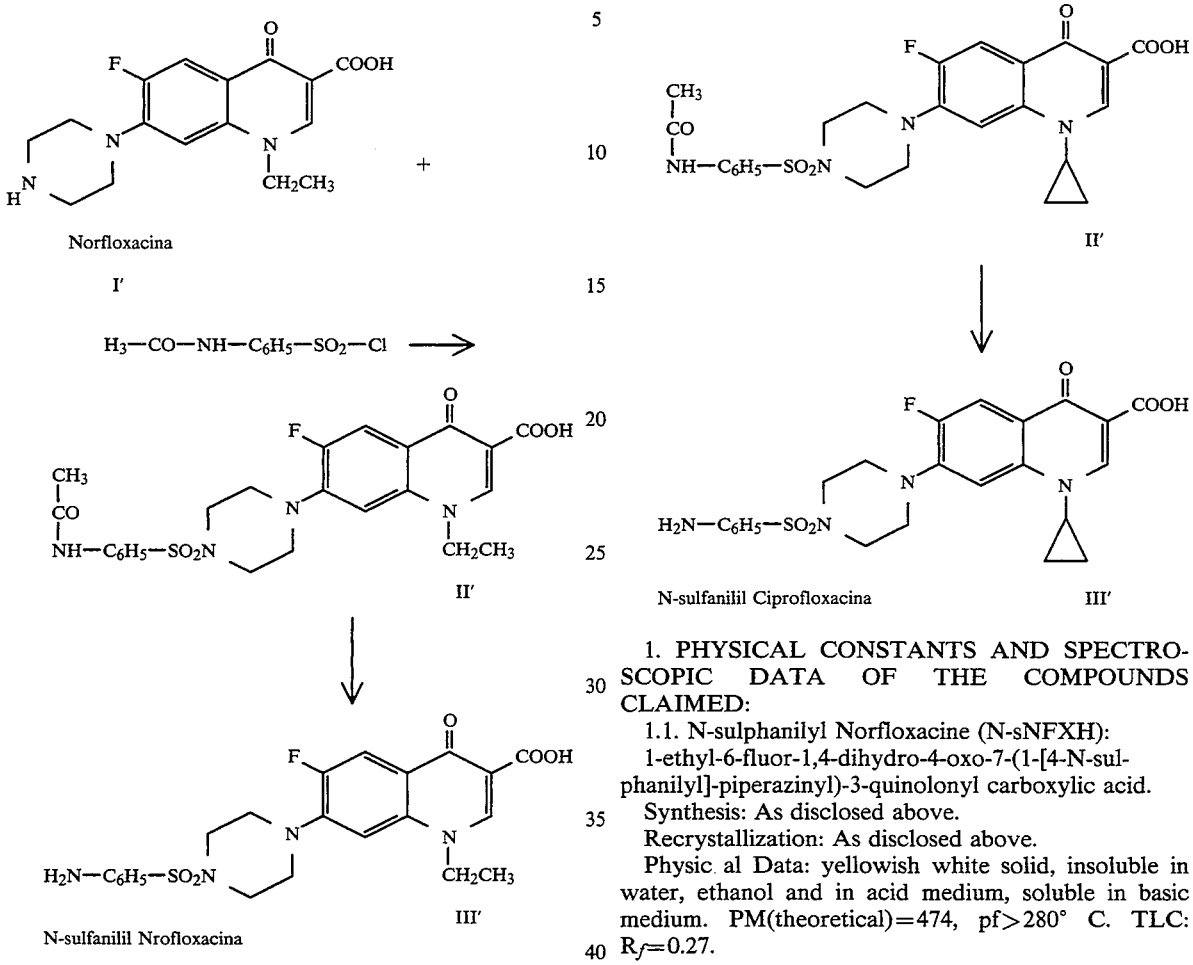

EXAMPLE 2

The compound (III), that is the 1-cyclopropyl-6-fluor-1,4-dihydro-7-(4-[(4-aminophenyl)sulphonyl]-1-piperazinyl)-4-oxo-3-quinoline carboxylic acid was obtained with a mol yield of 80% when compound (I) was the 1-cyclopropyl-6-fluor-1,4-dihydro-7-(1-piperazinyl)-4-oxo-3-quinoline carboxylic acid, INN 5024 (Ciprofloxacine) CAS 85721-33-1. The compound (III) was recrystallized from a mixture of dimethylformamide ethanol-water (5:5:1) with a yield of 95% producing a white solid insoluble in water, but soluble in solutions of alkaline hydroxides.

Assays

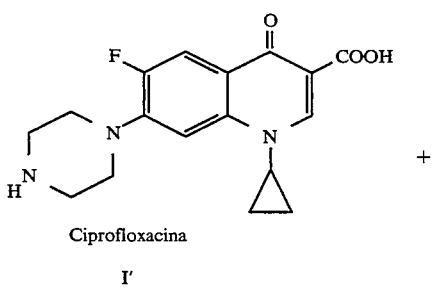

Ciprofloxacina

I'

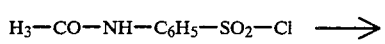

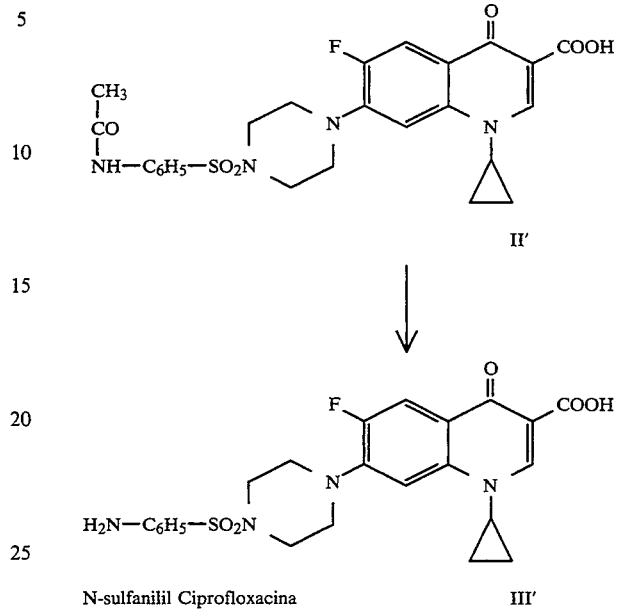

1. PHYSICAL CONSTANTS AND SPECTROSCOPIC DATA OF THE COMPOUNDS CLAIMED:

1.1. N-sulphanilyl Norfloxacine (N-sNFXH):
1-ethyl-6-fluor-1,4-dihydro-4-oxo-7-(1-[4-N-sulphanilyl]-piperazinyl)-3-quinolonyl carboxylic acid.
Synthesis: As disclosed above.
Recrystallization: As disclosed above.
Physic al Data: yellowish white solid, insoluble in water, ethanol and in acid medium, soluble in basic medium. PM(theoretical)=474, pf>280° C. TLC: $R_f$=0.27.

Spectroscopic Data

*IR Spectrum (BrK, cm$^{-1}$): 3490 (NH asymmetric), 3371 (NH symmetric), 1717 (C=O acid), 1611 (C=O ketone), 1150 (SO$_2$ symmetric), 872 (S-N).
*Mass Spectrum: m/z 472(22), 458(11), 318(17), 274(53), 233(4), 219(9), 56(100), 44(24).
*U.V. Spectrum: $\epsilon_{271}$ (water): 3.74×10$^4$, $\epsilon_{280}$ (ethanol): 4.45×10$^4$.

1.1.i. Sodium N-sulphanilyl Norfloxacine (N-sNFXH Na):
Sodium salt of the 1-ethyl-6-fluor-1,4-dyhidro-4-oxo-7-(1-[4-N-sulphanilyl]-piperazinyl)-3-quinolonyl carboxylic acid.
Synthesis: 1 gr of N-sNFXH is suspended in 50 ml of sodium hydroxide 1.5N in ethanol, and the reflux is maintained during 20 minutes. The insoluble yellowish white solid is isolated, then it is dried at 60° C. and at reduced pressure (<100 mm of Hg) during three hours, and is finally recrystallized from an ethanol-water mixture (10:1).
Physical Data: yellowish white solid, soluble in water, insoluble in ethanol. PM (theoretical)=496. TLC: $R_f$=0.31.

Spectroscopic Data

*IR Spectrum (BrK, cm$^{-1}$): 3374 (NH symmetric), 1618 (C=O carboxylic), 1153 (SO$_2$ symmetric).

1.2 N-sulphanilyl Ciprofloxacine (N-sCFXH):

1-cyclopropyl-6-fluor-1,4-dihydro-4-oxo-7-(1-[4-N-sulphanilyl]-piperazinyl)-3-quinolonyl carboxylic acid.

Synthesis: as disclosed above.

Recrystallization: as disclosed above.

Physical Data: yellowish white solid, insoluble in water, ethanol and in acid medium, soluble in basic medium. PM (theorical)=486, pf<280° C. TLC: $R_f=0.29$.

Spectroscopic Data

*IR Spectrum (BrK, cm$^{-1}$): 3470 (NH asymmetric), 3375 (NH symmetric), 1716 (C=O acid), 1610 (C=O ketone), 1148 (SO$_2$ symmetric).

*Mass Spectrum: m/z 486 (9), 442 (20), 330 (4), 286 (9), 56 (100), 44 (19).

1.2.i. Sodium N-sulphanilyl Ciprofloxacine (N-sCFXH Na):

Sodium salt of the 1-cyclopropyl-6-fluor-1,4-dihydro-4-oxo-7-(1-[4-N-sulphanilyl]-piperazinyl)-3-quinolonyl carboxylic acid.

Synthesis: 1 gr. of N-sCFXH is suspended in 50 ml of sodium hydroxide 1.5N in ethanol reflux is maintained during 20 minutes. The insoluble yellowish white solid is isolated and then it is dried at 80° C. and reduced pressure (<100 mm de Hg) during three hours, and finally is recrystallized from an ethanol-water mixture (10:1).

Physical Data: yellowish white solid, soluble in water, insoluble in ethanol.

PM (theorical)=508.

2. DETERMINATION OF THE ANTIBACTERIAL ACTIVITY "IN VITRO"

Assays "in vitro" CIM of the new derivatives, N-sNFXH (1.1.) and N-sCFXH (1.2.), which are original compounds not described in literature, to standard strains (ATCC, American Type Culture Colection) of Gram-negative and Gram-positive germs, have been carried out.

A slight decrease of the activity against Gram-negative germs (Escherichia coli and Pseudomonas aeruginosa) in comparison with its precursors, Ciprofloxacine (CFXH) and Norfloxacine (NFXH), is observed.

However, a significant increase of the activity of these compounds against Gram-positive germs like Staphylococcus aureus and Enterococcus faecalis is noticed; as is shown in the Table 2. Said increase is about 10 times for N-sNFXH (1.1.) and N-sCFXH (1.2).

TABLE 2

| Antibacterial activity of AAFQ to clinical strains. | | | | |
|---|---|---|---|---|
| Microorg. | Compound | Range | CIM50 | CIM90 |
| Staphylococcus aureus ATCC 25923 | NFXH | 0.5–1.0 | 0.5 | 1.0 |
| | N-sNFXH | 0.25 | 0.25 | 0.25 |
| | CFXH | 0.25 | 0.25 | 0.25 |
| | N-sCFXH | 0.03–0.06 | 0.03 | 0.06 |
| Staphylococcus aureus* | NFXH | 0.25–2.0 | 0.5 | 1.0 |
| | N-sNFXH | 0.06–0.5 | 0.125 | 0.125 |
| | CFXH | 0.125–2.0 | 0.25 | 0.5 |
| | N-sCFXH | 0.015–0.125 | 0.03 | 0.06 |
| Enterococcus faecalis ATCC 29212 | NFXH | 2.0 | 2.0 | 2.0 |
| | N-sNFXH | 0.5 | 0.5 | 0.5 |
| | CFXH | 1.0 | 1.0 | 1.0 |
| | N-sCFXH | 0.125 | 0.125 | 0.125 |
| Enterococcus faecalis* | NFXH | 4.0 | 4.0 | 4.0 |
| | N-sNFXH | 0.25 | 0.25 | 0.25 |
| | CFXH | 2.0 | 2.0 | 2.0 |

TABLE 2-continued

| Antibacterial activity of AAFQ to clinical strains. | | | | |
|---|---|---|---|---|
| Microorg. | Compound | Range | CIM50 | CIM90 |
| | N-sCFXH | 0.06 | 0.06 | 0.06 |

*Clinical strains obtained from different hospitals.

3. DETERMINATION "IN VITRO" OF PHARMACOKINETIC PARAMETERS OF THE N-sNFXH (1.1.) DERIVATIVE

The absorption of the N-sNFXH (1.1) was studied, in preliminary form, in animals of laboratory to obtain data of the pharmakinetic behavior of these new compounds. The obtained results are shown in the Table 3.

TABLE 3: Absorption of the NFXH(Norfloxacine) and the N-sNFXH(1.1.) in laboratory animals. Dosage 50 μg/kg.

| NFXH | | N-sNFXH | |
|---|---|---|---|
| Time min. | Concentration μg/ml | Time min. | Concentration μg/ml |
| 15 | 0.43 | 15 | 0.34 |
| 38 | 1.13 | 38 | 0.48 |
| 60 | 0.85 | 60 | 1.80 |
| | | 60 | 1.70 |
| 120 | 0.20 | 120 | 0.08 |

A maximum of absorption of 1.3 μg/ml is noticed in the case of the NFXH, after about forty minutes of being administered in a simple dosage and included in a vehicle to form a suspension, that was utilized as compound of reference.

A delay in the absorption can be noticed in comparison with the literature absorption data of the NFXH, where a maximum of concentration in blood of 1.59 μg/ml after fifteen minutes of being administered by oral via is observed, which can exactly be attributed to the difference in the formula. In this assay, the NFXH in suspension form (solid) needs an "extra" period of time to be dissolved and thus it is available to the absorption.

A maximum of concentration in blood of 1.8 μg/ml after about sixty minutes of being administered as a suspension in a simple dosage of 50 mg/kg is observed in the case of N-sNFXH (1.1.).

In summary, it can be said that the N-sNFXH is absorbed more slowly than the NFXH, which could be explained in terms of the low solubility that this derivative has in comparison with the NFXH.

However, the top of maximum concentration in blood is something greater in the case of the N-sNFXH, reaching a concentration of 1.8 μg/ml, in both cases the maximum concentrations attained exceed the necessary CIM to execute its antibacterial activity.

We claim:

1. A 7-(4-[4-aminophenyl)sulphonyl]-1-piperazinyl) fluorquinolonic derivative, having the formula:

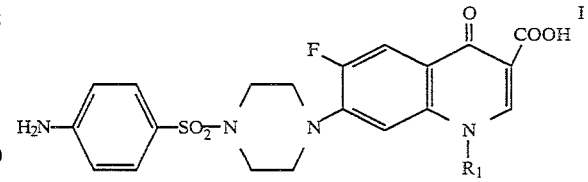

wherein R$_1$ represents C$_1$–C$_6$ alkyl.

2. A process for preparing 7-(4-[4-aminophenyl)sulphonyl]-1-piperazinyl) fluorquinolonic derivatives comprising: reacting 7-(1-piperazinyl) fluorquinolone or an ester thereof with N-acetylsulphanilyl chloride and hydrolyzing the ester and recovering the derivative.

* * * * *